United States Patent [19]

Brewer

[11] Patent Number: 4,845,217

[45] Date of Patent: Jul. 4, 1989

[54] PURIFICATION OF 5-PYRIMIDINECARBOXAMIDES

[75] Inventor: Arthur D. Brewer, Puslinch, Canada

[73] Assignee: Uniroyal Chemical Ltd./Ltee, Don Mills, Canada

[21] Appl. No.: 939,373

[22] Filed: Dec. 8, 1986

Related U.S. Application Data

[63] Continuation-in-part of Ser. No. 735,895, May 17, 1985, abandoned.

[51] Int. Cl.$^4$ ................. A61K 31/515; C07D 239/66; C07D 239/68
[52] U.S. Cl. ........................................ 544/301; 536/23
[58] Field of Search .................. 544/299, 301; 536/23

[56] References Cited

U.S. PATENT DOCUMENTS

| | | | |
|---|---|---|---|
| 3,961,061 | 6/1976 | Kramer et al. | 544/301 |
| 4,283,444 | 8/1981 | de Sousa et al. | 544/301 |
| 4,399,280 | 8/1983 | de Sousa et al. | 544/301 |
| 4,634,707 | 1/1987 | Brewer et al. | 544/301 |
| 4,636,508 | 1/1987 | Brewer | 544/301 |

Primary Examiner—Anton H. Sutto
Assistant Examiner—Mark W. Noel
Attorney, Agent, or Firm—John A. Shedden

[57] ABSTRACT

A process is provided for the purification to highly purified states of 5-pyrimidinecarboxamides which are essentially insoluble in both organic and inorganic solvents. The 5-pyrimidinecarboxamide to be purified is contacted with an organic base having a pKa value in excess of 6.95 to form an adduct. The adduct is purified through recrystallization and the desired 5-pyrimidinecarboxamide is regenerated from the adduct in highly purified form with acid. Additionally, an adduct resulting from the combination of a 5-pyrimidinecarboxamide with such an organic base is provided, which adduct is capable of being purified using recrystallization techniques, where the 5-pyrimidinecarboxamide is not itself capable of being so purified due to its relative insolubility in organic and inorganic solvents.

8 Claims, No Drawings

PURIFICATION OF 5-PYRIMIDINECARBOXAMIDES

CROSS-REFERENCE TO RELATED APPLICATION

This application is a continuation-in-part of copending application Ser. No. 735,895, filed May 17, 1985, now abandoned.

BACKGROUND OF THE INVENTION

This invention relates to the purification of 5-pyrimidinecarboxamides such as the 5-carboxamido or 5-thiocarboxamido derivatives of 2-thio- or 2-selenobarbituric acid disclosed in copending U.S. patent application Ser. No. 699,720 filed on Feb. 8, 1985 [593 KON-IIA], or the N-phenyl-5-carboxamide-2-thiobarbituric acid derivatives disclosed in copending U.S. patent application Ser. No. 699,776 filed on Feb. 8, 1985 [599 KON-IA], now U.S. Pat. No. 4,634,707 granted Jan. 6, 1987.

5-pyrimidinecarboxamides and related compounds have been purified using conventional techniques such as column chromatography or recrystallization. For example, U.S. Pat. No. 3,784,547 (Samour et al.), U.S. Pat. No. 3,999,974 (Hirono et al.), U.S. Pat. No. 4,460,588 (Serban et al.) and Japanese Patent Publication No. 1445/64 [39(1964)-1445]disclose such techniques for purifying various 5-substituted barbituric acids and other pyrimidine derivatives.

The 5-pyrimidinecarboxamides described in the aforesaid copending applications exhibit anti-leukemia and anti-tumor activity, and thus have potential pharmaceutical application. It has not, however, previously been possible to obtain such materials in chemically pure states. To the contrary, these compounds are difficult to handle and process, due to their extreme insolubility in organic or inorganic solvents. That insolubility precludes purification by recrystallization techniques such as described in the above patents or otherwise commonly utilized in preparative organic chemistry. Furthermore, these compounds are not easily purified by chromatographic techniques, which are in any case only applicable on a small scale, require expensive apparatus and highly trained personnel, and are of marginal efficacy and poor productivity. Since an exceptional degree of purity is mandated for an agent which is used therapeutically on human patients, the difficulty of purification of the 5-pyrimidinecarboxamides represents a serious problem in their development as anit-cancer drugs.

It is accordingly among the objects of the present invention to provide an improved process for the purification of a 5-pyrimidinecarboxamides, particularly those of the aforesaid copending applications, by which the desired compounds may be obtained in very high, pharmaceutical-grade purity on a bulk scale. Other objects and advantages of the invention will be apparent from the following detailed description of preferred forms of the invention.

SUMMARY OF THE INVENTION

The purification process of the present invention is applicable to purification of the 5-pyrimidinecarboxamides disclosed in the aforesaid copending applications, particularly 5-carboxamide-2-thiobarbituric acid derivatives described in the aforesaid application Ser. No. 699,776. These compounds have the formula: wherein

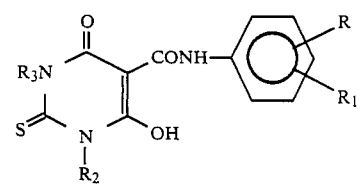

R is hydrogen, 2 or 3-halo, 2-methyl, 4-fluoro, 4-($C_1$-$C_6$ alkoxyl), 2 or 4-trifluoromethyl, or hydroxyl, and $R_1$ is hydrogen; or R is 2-fluoro and $R_1$ is 4-fluoro; or R is 2-methoxy and $R_1$ is 5-methyl; and $R_2$ and $R_3$ are hydrogen atoms or carbohydrate residues.

The carbohydrate residues may be furanosyl (e.g., ribofuranosyl), pyranosyl (e.g., arabinopyranosyl, glucopyranosyl, or galactopyranosyl), their deoxy derivatives, or their aliphatic analogs (e.g., hydroxyalkoxyalkyl or polyhydroxyalkyl groups having from 2 to 12 carbon atoms in each of the alkoyx and alkyl moieties thereof, such as 2-hydroxyethoxymethyl or 2,3-dihydroxypropyl. As used herein, the term "carbohydrate residue" is intended to refer to those cyclic and acyclic and acyclic groups specified hereinabove.

The 5-carboxamide-2-thiobarbituric acid derivatives purified in in accordance with the invention can exist in the form illustrated in the above formula or in any of its tautomeric forms.

In accordance with the invention, these 5-pyrimidinecarboxamides are purified by reacting them with a suitable organic base to form a corresponding adduct, purifying the adduct, and regenerating the 5-pyrimidinecarboxamide from the purified adduct with dilute acid. Surprisingly, adducts thus formed are readily purified, e.g., by recrystallization one or more times from a solvent in which there is substantial differential solubility with temperature, followed by regeneration of the original carboxamides in substantially chemically pure state. Moreover, the purification may be effected on a large scale without the necessity of high capital investment or processing costs.

DESCRIPTION OF THE PREFERRED EMBODIMENTS

In accordance with a preferred embodiment of the invention, a 5-pyrimidinecarboxamide is initially reacted with an organic base to form an adduct. Suitable organic bases are those bases having a pKa value greater than about 6.95, and preferably having a pKa value of at least about 7.4. Particularly suitable organic bases include alkylamines and alkanolamines having the formula $R_4R_5R_6N$ wherein at least one of $R_4$, $R_5$ or $R_6$ is an alkyl, substituted alkyl or hydrdoxyalkyl group having from 1 to 24 carbon atoms (preferably $C_1$-$C_{12}$), or two or three of the $R_4$, $R_5$, and $R_6$ groups form a basic nitrogen-containing heterocyclic moiety, and any remaining substituents are hydrogen. Examples of organic amines having pKa values greater than 6.95 which may be so utilized include monoalkylamines such as dodecylamine; trialkylamines such as triethylamine; trialkanolamines such as triethanolamine; and basic nitrogen-containing heterocyclic amines such as 2,6-dimethylmorpholine, piperidine or 2,4,6-trimethylpyridine. Other strong bases within the class of materials useful in the process of the present invention are those listed, for example, in the CRC Handbook of Chemistry and Physics, 65th. Edition, pp. D-163 to D-165.

The 5-pyrimidinecarboxamide and the base are suitably reacted in molar proportions varying from about 1:1 to 1:5, preferably from about 1:1 to 1:2, carboxamide to base. One-to-one adducts of the carboxamide are thereby formed.

The reaction is carried out by initially suspending the 5-pyrimidinecarboxamide in a relatively polar organic solvent. Solvents such as the lower ($C_1$–$C_5$) alcohols (e.g., ethanol, lower aliphatic ketones (e.g., methyl isobutyl ketone), heterocyclic ethers (e.g., 1,4-dioxane), heterocyclic solvents (e.g., pyridine or sulfolane), or mixtures thereof (e.g., ethanol and pyridine) have been found so useful.

The suspension is thereafter warmed and the organic base is added, forming the desired adduct which is partially soluble in the suspension. The suspension is then brought to boiling, desirably under gentle reflux, and additional solvent is added until all solids go into solution.

The adduct is thereafter purified by recrystallization. This is accomplished by cooling the adduct/solvent mixture until the purified adduct crystallizes, generally at a temperature of from about $+20°$ C. to $-20°$ C.

Finally, the purified adduct is treated with acid to regenerate the purified 5-pyrimidinecarboxamide therefrom. The regeneration is accomplished by triturating the purified adduct crystals with an acid having a pKa of less than about 6.5. Any of the strong mineral or organic acids, e.g., hydrochloric, sulfuric, nitric, acetic or propionic acids, may be thus utilized. The regenerated crystals are then washed with water. The purity of the regenerated 5-pyrimidinecarboxamide may then be determined, and the process repeated if a higher purity product is requried.

Depending on the 5-pyrimidinecarboxamide treated improved purities may be obtained by alternating the organic base and/or the solvent used during successive repetitions of the purifications operations.

It is particularly preferred to utilize the process of the invention for the purification of N-phenyl-5-carboxamide-2-thioarbituric acid, viz., 1,2,3,4-tetrahydro-6-hydroxy-4-oxo-N-phenyl-2-thioxo-5pyrimidinecarboxamide. Employing the present technique, that compound can be refined to purities approaching 100%. The following examples illustrate, but do not restrict, the purification of this and similar 5-pyrimidinecarboxamides, employing this process. Unless otherwise indicated, all parts and percentages specified in the examples are by weight, and all temperatures in degrees Celsius.

EXAMPLE 1

Purification of 1,2,3,4-Tetrahydro-6-hydroxy-4-oxo-N-Phenyl-2-Thioxo-5-Pyrimidinecarboxamide utilizing triethylamine Adduct A sample of 1,2,3,4-tetrahydro-6-hydroxy-4-oxo-N-phenyl-2-thioxo-5-pyrimidinecarboxamide was prepared as described in Example 1A of the aforesaid copending application Ser. No. 699,776. By high pressure liquid chromatography (HPLC) this sample was found to contain 96.1% of the carboxamide, i.e., it had a purity fo 96.1%; three other unidentified components (A, B and C) were present as impurities in amounts of 0.8, 2,7 and 0.4% by weight, respectively.

A sample of the semi-pure carboxamide was suspended in absolute ethanol, two equivalents of triethylamine were added, and the suspension was boiled, with the addition of ethanol, until all solids went into solution. On cooling to a temperature of 0° C., a crystalline solid appeared which was collected, washed with a little ethanol and triturated with dilute hydrochloric acid. The purified product was washed with water and dried; the desired carboxamide was obtained in 98.8% purity. The process was repeated twice, producing an intermediate product having a 99.2% purity and a final product having 99.7% purity.

EXAMPLE 2

Using the same semi-pure specimen as in Example 1, the procedure described in Example 1 swas repeated, using as the recrystallizing solvent a 50:50 mixture (by weight) of ethanol and pyridine. Two successive products having purities of 99.7% and 99.8% of the desired carboxamide were thus formed.

EXAMPLE 3

Adduct Formation with N-Triethanolamine

The procedure of Example 1 was followed with a further portion of the same initial sample, using two equivalents of triethanolamine in place of triethylamine. Successive products having 99.99% and 100% purities were thus obtained.

EXAMPLE 4

Adduct Formation with N-dodecylamine

The procedure of Example 1 was followed with an additional portion of the same sample, using two equivalents of n-dodecylamine in place of triethylamine. After a single purification, a product containing 99.96% of the carboxamide was obtained.

EXAMPLE 5 Successive Adduct Formation with Triethylamine and n-Dodecylamine

A further sample of 1,2,3,4-tetrahydro-6-hydroxy-4-oxo-N-phenyl-2-thioxo-5-pyrimidinecarboxamide was prepared as described in Example 1, but from a different batch; the initial purity, as assayed by HPLC, was 93.6%. This sample was then purified in the manner described in Example 1 above, using triethylamine to form the adduct initially crystallized, and n-dodecylamine to form a second adduct thereaftercrystallized. The product formed by trituration of the first adduct with HCl contained 99.94% of the carboxamide, while the product formed by trituration of the second adduct with HCl had a 99.98% purity.

EXAMPLE 6

Successive Adduct Formation with N-Dodecylamine and Triethylamine

Using a portion of the same sample treated in Example 5, the purification procedure described therein was repeated, using n-dodecylamine as the base to form the first adduct and triethylamine to form the second adduct. The successive products had purities of 99.9% and 99.95%.

EXAMPLE 7

Purification of
1,2,3,4-Tetrahydro-6-hydroxy-N-(2-Methylphenyl)-4-oxo-2-thioxo-5-Pyrimidinecarboxamide utilizing Triethylamine Adduct A specimen of 1,2,3,4-tetrahydro-6-hydroxy-N-(2-methylphenyl)-4-oxo-2-thioxo-5-pyrimidinecarboxamide was prepared in the manner described in Example 3 of copending application Ser. No. 699,766. The crude material had a 73.8% purity. It was treated with triethylamine and ethanol as described in Example 1. The purified product was chemically pure (100% purity).

EXAMPLE 8

Purification of
1,2,3,4-Tetrahydro-6-Hydroxy-N-(4-Methoxyphenyl)-4-oxo-2-Thioxo-5-Pyrimidinecarboxamide Utilizing Triethylamine Adduct A sample of 1,2,3,4-tetrahydro-6-hydroxy-N-(4-methoxyphenyl)-4-oxo-2-thioxo-5-pyrimidinecarboxamide was prepared as described in Example 6 of the aforesaid copending application. The sample was purified as described in Example 1 above except that dilute, 2 N sulfuric acid was substituted for hydrochloric acid. The product purity, determined by HPLC, was 100%.

EXAMPLE 9

A further sample of 1,2,3,4-tetrahydro-6-hydroxy-N-phenyl-4-oxo-2-thioxo-5-pyrimidinecarboxamide was prepared, in the same manner as previously described. The sample treated was 98% pure. The sample was suspended in ethanol (10 ml per gram), the suspension was warmed to 50° C., and triethylamine was added (1 g per gram of the semi-pure sample). The suspension was gently refluxed with stirring for 2 hours, and then reduced in volume in vacuo to a solid. The suspension was then recrystallized from boiling ethanol; the hot solution was filtered and chilled, giving a cropof greenish needles which were collected and dried. This solid was thoroughly triturated with an excess of dilute (3 N) HCl. The white solids so produced were filtered and washed with water until the washings no longer had an acid reaction. It was then dried. The resulting product was substantially pure.

EXAMPLE 10

Purification of
N-(2-Chlorophneyl)-1,2,3,4-Tetrahydro-6-Hydroxy-4-oxo-2-Thioxo-5-Pyrimidinecarboxamide The named compouond was prepared as described in Example 2 of the aforesaid Ser. No. 699,776, and converted to the triethylamine adduct in the manner described in Example 1 above. The product thus formed (Sample A) was recrystallized twice from ethanol (Samples B and C):

| Sample | % of Impurity | % of Final Product |
|--------|---------------|--------------------|
| A | 3.5 | 96.5 |
| B | 1.7 | 98.3 |
| C | 0.8 | 99.2 |

EXAMPLE 11

Adduct Formtion with Heterocyclic Bases

Adducts of 1,2,3,4-tetrahydro-6-hydroxy-4-oxo-N-phenyl-2-thioxo-5-pyrimidinecarboxamide were formed with 2,6-dimethylmorpholine and 2,4,6-trimethylpyridine (pKa=7.43); and adducts of its 4-ethoxy analog (1,2,3,4-tetra-hydro-6-hydroxy-4-oxo-N-4-ethoxyphenyl-2-thioxo-5-pyrimidine- carboxamide) were formed with 2,6-dimethylmorpholine and hexamethylenimine, as follows:

The pyrimidinecarboxamides and the respective bases (in 2-3 fold the stoichiometric quantities) were added thereto. The mixtures were gently warmed for 1/2 hour, cooled and the resulting solids collected and washed thoroughly with cold ethanol. (The free, unreacted bases were soluble in ethanol and were removed by washing to the extent unreacted.) The solids were examined by NMR. The bases were present in 1:1 molar ratios with the carboxamides, indicating the formation of the discrete salts.

When a further sample of the unsubstituted pyrimidinecarboxamide (1,2,3,4-tetrahydro-6-hydroxy-4-oxo-N-phenyl2-thioxo-5-pyrimidinecarboxamide) was reacted in the same manner with imidazole (pKa=6.95), the solid product contained no base, indicating the absence of adduct formation.

The following table summarizes the analyses of the samples treated and the various intermediate and final purified products formed in the above examples, the various impurities detected (by HPLC) being identified as Impurities A-E, respectively:

| ANALYSES OF PURIFICATION EXAMPLES | | | | | | |
|---|---|---|---|---|---|---|
| | Carboxamide Content (Wt. %) [Purity] | Impurity Content (Wt. %) | | | | |
| | | A | B | C | D | E |
| Example 1 | | | | | | |
| Raw Specimen | 96.1 | 0.8 | 2.7 | 0.4 | — | — |
| First Intermediate Purified Product | 98.8 | 0.6 | 0.3 | 0.3 | — | — |
| Second Intermediate Purified Product | 99.2 | 0.3 | 0.2 | 0.3 | — | — |
| Final Purified Product | 99.7 | — | — | 0.3 | — | — |
| Example 2 | | | | | | |
| Raw Specimen | 96.1 | 0.8 | 2.7 | 0.4 | — | — |
| Intermediate Purified Product | 99.7 | — | — | 0.3 | — | — |
| Final Intermediate Purified Product | 99.8 | — | — | 0.2 | — | — |
| Example 3 | | | | | | |
| Raw Specimen | 96.1 | 0.8 | 2.7 | 0.4 | — | — |
| Intermediate Purified Product | 99.9 | — | 0.01 | — | — | — |
| Final Intermediate Purified Product | 100 | — | — | — | — | — |
| Example 4 | | | | | | |
| Raw Specimen | 96.1 | 0.8 | 2.7 | 0.4 | — | — |
| Final Purified Product | 99.96 | — | — | 0.04 | — | — |
| Example 5 | | | | | | |
| Raw Specimen | 93.6 | — | 6.4 | — | — | — |
| Intermediate Purified Product | 99.94 | — | 0.06 | — | — | — |
| Final Intermediate Purified Product | 99.98 | — | 0.02 | — | — | — |
| Example 6 | | | | | | |
| Raw Specimen | 93.6 | — | 6.4 | | | |
| Intermediate Purified Product | 99.90 | — | 0.10 | — | — | — |
| Final Intermediate Purified Product | 99.95 | — | 0.05 | — | — | — |

-continued

ANALYSES OF PURIFICATION EXAMPLES

| | Carboxamide Content (Wt. %) [Purity] | Impurity Content (Wt. %) | | | | |
|---|---|---|---|---|---|---|
| | | A | B | C | D | E |
| Example 7 | | | | | | |
| Raw Specimen | 73.8 | 1.6 | 24.4 | — | 0.2 | — |
| Intermediate Purified Product | 100 | — | — | — | — | — |
| Example 8 | | | | | | |
| Raw Specimen | 99.5 | — | — | — | — | 0.5 |
| Purified Product | 100 | — | — | — | — | — |

What is claimed is:

1. A process for purifying a 5-pyrimidine-carboxamide of the formula:

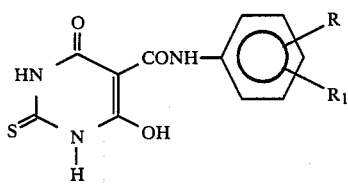

wherein
R is hydrogen, 2 or 3-halo, 2-methyl, 4-fluoro, 4-($C_1$-$C_6$ alkoxyl), 2 or 4-trifluoromethyl, or hydroxyl, and $R_1$ is hydrogen; or
R is 2-fluoro and $R_1$ is 4-fluoro; or
R is 2-methoxyl and $R_1$ is 5-methyl; which consists essentially of
(a) reacting the impure 5-pyrimidinecarboxamide with a pharmaceutically inert organic base having a pKa greater than 6.95 to form a crystalline adduct thereof;
(b) dissolving the adduct in a solvent and cooling to recrystallize the adduct; and
(c) treating the recrystallized adduct with acid to regenerate the 5-pyrimidinecarboxamide in substantially pure form.

2. The process according to claim 1, wherein the adduct is recrystallized from a polar organic solvent in which the adduct is substantially more soluble when the solvent is heated than under ambient conditions.

3. The process according to claim 2, wherein the 5-pyrimidinecarboxamide is 1,2,3,4-tetrahydro-6-hydroxy-4-oxo-N-phenyl-2-thioxo-5-pyrimidinecarboxamide.

4. The process according to claim 2, wherein the 5-pyrimidinecarboxamide is 1,2,3,4-tetrahydro-6-hydroxy-N-(2-methylphenyl)-4-oxo-2-thioxo-5-pyrimidinecarboxamide.

5. The process according to claim 2, wherein the 5-pyrimidinecarboxamide is 1,2,3,4-tetrahydro-6-hydroxy-N-(4-methoxyphenyl)-4-oxo-2-thioxo-5-pyrimidinecarboxamide.

6. The process according to claim 1, wherein the pKa value of the pharmaceutically inert organic base is at least 7.4.

7. The process of claim 1, wherein the organic base is an alkylamine or alkanolamine having the formula $R_4R_5R_6N$, wherein at least one of $R_4$, $R_5$ and $R_6$ is an alkyl or hydroxyalkyl group having from 1 to 12 carbon atoms, or two or three of the $R_4$, $R_5$ and $R_6$ groups form a basic nitrogen-containing heterocyclic moiety.

8. The process according to claim 2, wherein:
step (a) comprises suspending the 5-pyrimidinecarboxamide in said polar organic solvent, adding an organic base having a pKa greater than 6.95, of the formula $R_4R_5R_6N$, wherein at least one of $R_4$, $R_5$ and $R_6$ is an alkyl or hydroxyalkyl group having from 1 to 12 carbon atoms, or two or three of the $R_4$, $R_5$, and $R_6$ groups form a basic nitrogen- containing heterocyclic moiety, and the remaining substituents are hydrogen, to the resulting suspension with stiring, and warming the suspension to form a 1:1 adduct with the 5-pyrimidinecarboxamide, boiling the suspension, and dissolving the adduct in a solvent.
step (b) comprises cooling the solvent/adduct mixture to crystallize the adduct, and isolating the adduct crystals, and
step (c) comprises triturating the adduct crystals with an acid having a pKa less than 6.5, and drying the 5-pyrimidinecarboxamide crystals.

* * * * *